United States Patent
Klima et al.

(10) Patent No.: US 10,667,907 B2
(45) Date of Patent: Jun. 2, 2020

(54) SYSTEMS AND METHODS FOR DEVICE IMPLANTATION

(71) Applicant: St. Jude Medical, Cardiology Division, Inc., St. Paul, MN (US)

(72) Inventors: Daniel J. Klima, Andover, MN (US); Peter J. Ness, Minneapolis, MN (US); Mitchell F. McBride, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 311 days.

(21) Appl. No.: 15/592,538

(22) Filed: May 11, 2017

(65) Prior Publication Data

US 2017/0325953 A1 Nov. 16, 2017

Related U.S. Application Data (60) Provisional application No. 62/335,876, filed on May 13, 2016.

(51) Int. Cl.
*A61F 2/24* (2006.01)
*A61F 2/966* (2013.01)

(52) U.S. Cl.
CPC ............ *A61F 2/2436* (2013.01); *A61F 2/966* (2013.01); *A61F 2/2418* (2013.01); *A61F 2230/0067* (2013.01); *A61F 2250/0039* (2013.01)

(58) Field of Classification Search
CPC .......... A61F 2/2427; A61F 2/95; A61F 2/962; A61F 2/966; A61F 2002/2436; A61F 2002/9517
See application file for complete search history.

(56) References Cited

U.S. PATENT DOCUMENTS

| 4,423,730 A | 1/1984 | Gabbay |
| 4,471,777 A | 9/1984 | McCorkle, Jr. |

(Continued)

FOREIGN PATENT DOCUMENTS

| DE | 102004062296 A1 | 7/2006 |
| EP | 1129744 A1 | 9/2001 |

(Continued)

OTHER PUBLICATIONS

European Notice of Opposition between Proprietor: St. Jude Medical, Cardiology Division, Inc. and Opponent: Boston Scientific Corporation for European Patent No. EP2866738 dated May 17, 2017, Reference No. 31316-0061OP1, 29 pages.

(Continued)

*Primary Examiner* — Todd J Scherbel
(74) *Attorney, Agent, or Firm* — Lerner, David, Littenberg, Krumholz & Mentlik, LLP (57) ABSTRACT

An implantable delivery system has an inner shaft (20) with a device-carrying region (28) and an outer shaft (40) surrounding the inner shaft. A sheath (41) at a distal end of the outer shaft covers the device-carrying region when the outer shaft is in an advanced position. A sleeve (50) surrounding the outer shaft is in proximity to the sheath when the sleeve is in an advanced position. After insertion, the sleeve is retracted to increase flexibility of the distal end of the device. A handle (62) includes a control element for retracting the outer shaft and sheath relative to the inner shaft to release the implantable device. The sleeve may be fixed to the body of the handle when the sleeve is retracted. Engagement between the sleeve and an introducer at the insertion site can stabilize the handle and inner shaft against movement relative to the patient during retraction of the outer shaft.

10 Claims, 4 Drawing Sheets

(56) References Cited

U.S. PATENT DOCUMENTS

| | | | |
|---|---|---|---|
| 4,546,759 A | 10/1985 | Solar | |
| 4,575,371 A | 3/1986 | Nordqvist et al. | |
| 5,090,958 A | 2/1992 | Sahota | |
| 5,120,299 A | 6/1992 | Lombardi | |
| 5,201,901 A | 4/1993 | Harada et al. | |
| 5,334,160 A | 8/1994 | Ellis | |
| 5,411,552 A | 5/1995 | Andersen et al. | |
| 5,733,325 A | 3/1998 | Robinson et al. | |
| 5,766,151 A | 6/1998 | Valley et al. | |
| 5,795,325 A | 8/1998 | Valley et al. | |
| 5,797,952 A | 8/1998 | Klein | |
| 5,827,324 A | 10/1998 | Cassell et al. | |
| 5,868,706 A | 2/1999 | Cox | |
| 5,868,755 A | 2/1999 | Kanner et al. | |
| 5,924,424 A | 7/1999 | Stevens et al. | |
| 5,968,068 A | 10/1999 | Dehdashtian et al. | |
| 5,980,533 A | 11/1999 | Holman | |
| 6,051,014 A | 4/2000 | Jang | |
| 6,077,295 A | 6/2000 | Limon et al. | |
| 6,139,517 A | 10/2000 | Macoviak et al. | |
| 6,146,415 A * | 11/2000 | Fitz | A61F 2/95 606/171 |
| 6,190,357 B1 | 2/2001 | Ferrari et al. | |
| 6,214,036 B1 | 4/2001 | Letendre et al. | |
| 6,231,588 B1 | 5/2001 | Zadno-Azizi | |
| 6,306,141 B1 | 10/2001 | Jervis | |
| 6,312,407 B1 | 11/2001 | Zadno-Azizi et al. | |
| 6,361,545 B1 | 3/2002 | Macoviak et al. | |
| 6,375,668 B1 | 4/2002 | Gifford et al. | |
| 6,482,228 B1 | 11/2002 | Norred | |
| 6,592,612 B1 | 7/2003 | Samson et al. | |
| 6,607,551 B1 | 8/2003 | Sullivan et al. | |
| 6,623,518 B2 | 9/2003 | Thompson et al. | |
| 6,673,040 B1 | 1/2004 | Samson et al. | |
| 6,776,791 B1 | 8/2004 | Stallings et al. | |
| 7,235,095 B2 | 6/2007 | Haverkost et al. | |
| 8,414,644 B2 | 4/2013 | Quadri et al. | |
| 8,608,792 B2 | 12/2013 | Silveira et al. | |
| 8,641,749 B2 | 2/2014 | Barthold et al. | |
| 2002/0120323 A1 | 8/2002 | Thompson et al. | |
| 2003/0014007 A1 | 1/2003 | Eidenschink et al. | |
| 2003/0023265 A1 | 1/2003 | Forber | |
| 2003/0199963 A1 | 10/2003 | Tower et al. | |
| 2004/0087900 A1 | 5/2004 | Thompson et al. | |
| 2004/0093063 A1 | 5/2004 | Wright et al. | |
| 2004/0204749 A1 | 10/2004 | Gunderson | |
| 2004/0236406 A1 | 11/2004 | Gregorich | |
| 2004/0267346 A1 | 12/2004 | Shelso | |
| 2004/0267348 A1 | 12/2004 | Gunderson et al. | |
| 2005/0020974 A1 | 1/2005 | Noriega et al. | |
| 2005/0027345 A1 | 2/2005 | Horan et al. | |
| 2005/0033398 A1 | 2/2005 | Seguin | |
| 2005/0049667 A1 | 3/2005 | Arbefeuille et al. | |
| 2005/0049674 A1 | 3/2005 | Berra et al. | |
| 2005/0065590 A1 | 3/2005 | Shelso | |
| 2005/0090890 A1 | 4/2005 | Wu et al. | |
| 2005/0222662 A1 | 10/2005 | Thompson et al. | |
| 2006/0058865 A1 | 3/2006 | Case et al. | |
| 2006/0100688 A1 | 5/2006 | Jordan et al. | |
| 2006/0106415 A1 | 5/2006 | Gabbay | |
| 2006/0111771 A1 | 5/2006 | Ton et al. | |
| 2006/0142848 A1 | 6/2006 | Gabbay | |
| 2006/0149294 A1 | 7/2006 | Argentine et al. | |
| 2006/0167468 A1 | 7/2006 | Gabbay | |
| 2006/0195184 A1 | 8/2006 | Lane et al. | |
| 2006/0259120 A1 | 11/2006 | Vongphakdy et al. | |
| 2006/0276872 A1 | 12/2006 | Arbefeuille et al. | |
| 2007/0027534 A1 | 2/2007 | Bergheim et al. | |
| 2007/0073391 A1 | 3/2007 | Bourang et al. | |
| 2007/0088431 A1 | 4/2007 | Bourang et al. | |
| 2007/0106364 A1 | 5/2007 | Buzzard et al. | |
| 2007/0112422 A1 | 5/2007 | Dehdashtian | |
| 2007/0129749 A1 | 6/2007 | Thomas | |
| 2007/0142858 A1 | 6/2007 | Bates | |
| 2007/0162100 A1 | 7/2007 | Gabbay | |
| 2007/0168013 A1 | 7/2007 | Douglas | |
| 2007/0203561 A1 | 8/2007 | Forster et al. | |
| 2007/0203575 A1 | 8/2007 | Forster et al. | |
| 2007/0233224 A1 | 10/2007 | Leynov et al. | |
| 2007/0239271 A1 | 10/2007 | Nguyen | |
| 2007/0293930 A1 | 12/2007 | Wang et al. | |
| 2007/0293942 A1 | 12/2007 | Mirzaee | |
| 2008/0103443 A1 | 5/2008 | Kabrick et al. | |
| 2008/0114442 A1 | 5/2008 | Mitchell et al. | |
| 2008/0114443 A1 | 5/2008 | Mitchell et al. | |
| 2008/0140189 A1 | 6/2008 | Nguyen et al. | |
| 2008/0147182 A1 | 6/2008 | Righini et al. | |
| 2008/0221666 A1 | 9/2008 | Licata et al. | |
| 2008/0228255 A1 | 9/2008 | Rust et al. | |
| 2008/0255662 A1 | 10/2008 | Stacchino et al. | |
| 2008/0262590 A1 | 10/2008 | Murray | |
| 2008/0319526 A1 | 12/2008 | Hill et al. | |
| 2009/0054975 A1 | 2/2009 | del Nido et al. | |
| 2009/0143851 A1 | 6/2009 | Paul, Jr. | |
| 2009/0204197 A1 | 8/2009 | Dorn et al. | |
| 2009/0222035 A1 | 9/2009 | Schneiderman | |
| 2009/0228093 A1 | 9/2009 | Taylor et al. | |
| 2009/0240320 A1 | 9/2009 | Tuval et al. | |
| 2009/0259306 A1 | 10/2009 | Rowe | |
| 2009/0276027 A1 | 11/2009 | Glynn | |
| 2009/0281610 A1 | 11/2009 | Parker | |
| 2009/0287290 A1 | 11/2009 | Macaulay et al. | |
| 2010/0070015 A1 | 3/2010 | Schneider et al. | |
| 2010/0131039 A1 | 5/2010 | Chau et al. | |
| 2010/0145438 A1 | 6/2010 | Barone | |
| 2010/0152834 A1 | 6/2010 | Hannes et al. | |
| 2010/0268315 A1 | 10/2010 | Glynn et al. | |
| 2010/0274187 A1 | 10/2010 | Argentine | |
| 2010/0312325 A1 | 12/2010 | Dorn | |
| 2011/0029065 A1 | 2/2011 | Wood et al. | |
| 2011/0077731 A1 | 3/2011 | Lee et al. | |
| 2011/0078350 A1 | 3/2011 | Carls | |
| 2011/0098805 A1 | 4/2011 | Dwork et al. | |
| 2011/0137401 A1 | 6/2011 | Dorn et al. | |
| 2011/0137402 A1 * | 6/2011 | Dorn | A61F 2/95 623/1.12 |
| 2011/0172764 A1 | 7/2011 | Badhwar | |
| 2011/0224678 A1 | 9/2011 | Gabbay | |
| 2011/0251665 A1 | 10/2011 | Schmitt et al. | |
| 2011/0251666 A1 | 10/2011 | Schmitt et al. | |
| 2011/0251679 A1 | 10/2011 | Wiemeyer et al. | |
| 2011/0257720 A1 | 10/2011 | Peterson et al. | |
| 2011/0264201 A1 | 10/2011 | Yeung et al. | |
| 2011/0264202 A1 | 10/2011 | Murray, III et al. | |
| 2011/0288636 A1 | 11/2011 | Rolando et al. | |
| 2011/0301685 A1 | 12/2011 | Kao | |
| 2012/0078350 A1 | 3/2012 | Wang et al. | |
| 2012/0123528 A1 | 5/2012 | Knippel et al. | |
| 2012/0179033 A1 | 7/2012 | Merhi | |
| 2013/0116654 A1 | 5/2013 | Dehdashtian et al. | |
| 2013/0131775 A1 | 5/2013 | Hadley et al. | |
| 2013/0204344 A1 | 8/2013 | Tatalovich et al. | |
| 2013/0274860 A1 | 10/2013 | Argentine | |
| 2014/0005768 A1 | 1/2014 | Thomas et al. | |

FOREIGN PATENT DOCUMENTS

| | | |
|---|---|---|
| EP | 1157673 A2 | 11/2001 |
| WO | 9620025 A1 | 7/1996 |
| WO | 9748343 A1 | 12/1997 |
| WO | 990065418 A1 | 12/1999 |
| WO | 2006069704 A2 | 7/2006 |
| WO | 2006124549 A1 | 11/2006 |
| WO | 2007002863 A2 | 1/2007 |
| WO | 2007134290 A2 | 11/2007 |
| WO | 2008031103 A2 | 3/2008 |
| WO | 2008097556 A1 | 8/2008 |
| WO | 2009062955 A1 | 5/2009 |
| WO | 2009091509 A1 | 7/2009 |
| WO | 2009108942 A1 | 9/2009 |
| WO | 2010005524 A2 | 1/2010 |
| WO | 2010022138 A2 | 2/2010 |
| WO | 2010051025 A1 | 5/2010 |
| WO | 2010087975 A1 | 8/2010 |

(56) References Cited

FOREIGN PATENT DOCUMENTS

| WO | 2011025945 A1 | 3/2011 |
|---|---|---|
| WO | 2012009006 A1 | 1/2012 |
| WO | 2012036740 A2 | 3/2012 |
| WO | 2012038550 A1 | 3/2012 |

OTHER PUBLICATIONS

European Notice of Opposition between Proprietor: St. Jude Medical, Cardiology Division, Inc. and Opponent: Hepp Wenger Ryffel AG for European Patent No. EP2866738 dated May 16, 2017, Reference No. SSYME1704, 25 pages.
International Search Report and Written Opinion for Application No. PCt/US2011/001218 dated Nov. 11, 2011.
International Search Report and Written Opinion for Application No. PCT/US2012/047283 dated Oct. 30, 2012.
International Search Report and Written Opinion for Application No. PCT/US2013/047891 dated Dec. 4, 2013.
International Search Report and Written Opinion for Application No. PCT/US2013/048413 dated Dec. 4, 2013.
International Search Report dated Feb. 2, 2012 for Application No. PCT/US2011/001446.
International Search Report for Application No. PCT/US2011/001596 dated May 8, 2012.
Japanese Office Action for Application No. 2013-519648 dated Jun. 30, 2015.

* cited by examiner

SYSTEMS AND METHODS FOR DEVICE IMPLANTATION

CROSS REFERENCE TO RELATED APPLICATIONS

This application claims the benefit of the filing date of U.S. Provisional Patent Application No. 62/335,876 filed May 13, 2016, the disclosure of which is hereby incorporated by reference.

BACKGROUND OF THE INVENTION

The present invention relates to systems and methods for implanting a medical device within the cardiovascular system of a subject such as a human patient.

Medical devices such as prosthetic heart valves and stents commonly are inserted by a transluminal insertion procedure. One such procedure uses a delivery system including an inner shaft surrounded by an outer shaft. The implantable device is carried on the inner shaft near a distal end of the shaft. The outer shaft has a sheath at its distal end. A proximal end of the inner shaft is fixed to the body of a handle. The outer shaft may be connected to a mechanism within the handle body. The mechanism normally holds the outer shaft in fixed position relative to the handle body, but can actuated by a control element such as a thumb wheel, lever or the like may be provided on the handle to move the outer shaft and the sheath in the proximal and distal directions relative to the inner shaft.

A guidewire is placed into the subject's vasculature through an entry point where a blood vessel can be accessed conveniently. For example, where a device is to be implanted in or near the heart, the entry point may be at the femoral artery in the subject's leg. A hollow cannula referred to as an introducer is provided around the guidewire at the entry point. The introducer cannula typically incorporates an elastomeric seal to limit blood loss during the procedure.

The implantable device is loaded onto the inner shaft, and the sheath and outer shaft of the delivery system are moved to an advanced position in which the sheath covers the device. The delivery system is advanced over the guidewire and through the elastomeric seal of the introducer and into the subject's vasculature. The delivery system is advanced through the vasculature until the device is disposed at the desired implantation site. For example, the physician may determine that the delivery system is positioned properly by observing the subject under fluoroscopic imaging and determining that an alignment marker on the delivery system or the implantable device is disposed at the proper location relative to the subject's anatomy. Once the delivery system is at the proper location, the physician attempts to hold the handle stationary while actuating the control element of the handle to retract the outer shaft and the sheath proximally relative to the inner shaft and the device. Where the device includes a self-expanding stent, the device will expand as the sheath is retracted. This action detaches the device from the delivery system and implants it in the subject.

In such a procedure, the delivery system must bend to follow the path of the guidewire through the subject's vasculature. For example, where a prosthetic heart valve is to be delivered to the vicinity of the aortic annulus of the heart, the distal end of the delivery system must bend around the arch of the aorta. To allow sufficient flexibility, the outer shaft typically has a diameter smaller than the diameter of the sheath. For example, for implantation of some prosthetic heart valves, the sheath has an outer diameter of about 18 French catheter size (about 6 mm) to provide sufficient space to accommodate the valve in its collapsed condition, whereas the outer shaft has a diameter of about 14 French catheter size (about 4.3 mm). To provide reasonable sealing against blood loss, the elastomeric seal in the introducer sheath must be sufficiently resilient to accommodate these different diameters as they are passed through the seal. Frictional engagement between the seal and the outer shaft impedes the advancing motion of the delivery system. Moreover, when the physician actuates the control element on the handle to move the outer shaft and sheath relative to the inner shaft, the frictional engagement between the introducer and the outer shaft tends to hold the outer shaft stationary relative to the subject. Thus, the handle and the inner shaft tend to move relative to the subject while the device is being exposed. This displaces the device from the desired position.

Certain delivery systems disclosed in U.S. Published Patent Application No. 2014/0005768 A1, the disclosure of which is hereby incorporated by reference herein, incorporate a sleeve that fits around the outside of the outer shaft. The sleeve has an inner diameter just slightly larger than the outer diameter of the outer shaft to provide a close but freely slideable fit. Such a device can be used in the same manner as discussed above. However, when the delivery system is advanced through the introducer, the sleeve stops at the introducer so that the sleeve seals against the elastomeric seal. The physician can continue to advance the outer and inner shafts as discussed above to position the device. The relatively close fit between the sleeve and the outer shaft impedes blood loss through this space. However, still further improvement would be desirable.

SUMMARY

One aspect of the invention provides a delivery system for an implantable medical device. The delivery system desirably includes an elongated inner shaft having a device-carrying region adjacent a distal end thereof and an elongated, hollow outer shaft surrounding the inner shaft. A sheath desirably is mounted at a distal end of the outer shaft. The sheath preferably has an outside diameter greater than an outside diameter of the outer shaft. The outer shaft preferably is movable relative to the inner shaft in a proximal direction from an advanced position in which the sheath surrounds the device-carrying region of the inner shaft to a retracted position in which the sheath does not cover the device-carrying region. The system according to this aspect of the invention preferably includes a sleeve shorter than the outer shaft, the sleeve surrounding the outer shaft. The sleeve desirably is movable relative to the outer shaft from an advanced position in which a distal end of the sleeve is in close proximity to the proximal end of the sheath to a fully retracted position in which the distal end of the sleeve is remote from the sheath. Preferably, when the sleeve is in the advanced position, the distal end of the sleeve and the sheath cooperatively define a smooth exterior surface.

A further aspect of the present invention also provides a delivery system for an implantable medical device. The delivery system according to this aspect of the invention desirably includes an elongated inner shaft having a device-carrying region adjacent a distal end thereof and an elongated, hollow outer shaft surrounding the inner shaft. The system desirably includes a sheath mounted at a distal end of the outer shaft, the sheath having an outside diameter greater than an outside diameter of the outer shaft. Desirably, the outer shaft is movable relative to the inner shaft in a proximal direction from an advanced position in which the sheath surrounds the device-carrying region of the inner shaft to a retracted position in which the sheath does not cover the device-carrying region. The system according to this aspect of the invention desirably includes a sleeve shorter than the outer shaft surrounding the outer shaft, the sleeve being movable in a proximal direction relative to the outer shaft from an advanced position to a fully retracted position in which the distal end of the sleeve is remote from the sheath. Preferably, the system according to this aspect of the invention includes a handle having a body and a first control element, the inner shaft being fixed to the body, the outer shaft being movable relative to the inner shaft responsive to movement of the control element relative to the body by an operator. Desirably, the system further includes a catch operable to selectively fix the sleeve to the body of the handle against proximal and distal movement relative to the body when the sleeve is in the fully retracted position. For example, the sleeve may include a hub fixed to the sleeve adjacent its proximal end, and the hub and catch may be engageable with one another to fix the sleeve to the body of the handle. As further discussed below, frictional engagement of the sleeve with an introducer or with the patient's tissues near the insertion site tends to hold the sleeve in position relative to the patient. When the sleeve is fixed to the handle, this helps to keep the handle body and hence the inner shaft in place relative to the patient, and thus helps to prevent movement of the handle body and inner shaft relative to the patient during retraction of the outer shaft.

Yet another aspect of the invention provides a method of delivering an implantable medical device into the vasculature of a subject. A method according to this aspect of the invention desirably includes the step of advancing a delivery system into the vasculature of the subject at an entry location while maintaining a distal end of a sleeve surrounding an outer shaft of the delivery system in close proximity with a sheath mounted to the outer shaft so that the sleeve and sheath cooperatively define a smooth outer surface at least until the distal end of the sleeve enters the vasculature. For example, the delivery system may be advanced over a guidewire. The method desirably includes the steps of further advancing the outer shaft of the delivery system into the vasculature so that the outer shaft advances relative to the sleeve and then retracting the outer shaft and sheath relative to the sleeve and relative to an inner shaft carrying the implantable device so as to expose the implantable device. In preferred methods according to this aspect of the present invention, the smooth surface defined by the sleeve and sheath facilitates passage of the system into the vasculature as, for example, passage through an introducer having a seal.

Yet another aspect of the invention provides a further method of delivering an implantable medical device into the vasculature of a subject. The method according to this aspect of the invention desirably includes the step of advancing a delivery system into the vasculature of the subject through an entry location on the body of the subject while a sleeve surrounds an outer shaft of the delivery system, the advancing step being continued at least until a distal end of the sleeve enters the vasculature and engages either tissue of the subject at the entry location or a hemostatic seal of an introducer at the entry location. The method desirably includes locking an the inner shaft of the delivery system to the sleeve after the initial advancing step, the inner shaft being disposed within the outer shaft and carrying the implantable device. The method desirably includes retracting the outer shaft relative to the sleeve and relative to the inner shaft carrying the implantable device after the locking step so as to expose the implantable device. For example, the step of locking the inner shaft to the sleeve may be performed by locking a handle body fixed to the inner shaft to the sleeve the step of retracting the outer shaft may be performed by actuating a control element to move the outer shaft relative to the handle.

DETAILED DESCRIPTION

The terms "distal" and "distally" as used in this disclosure with reference to a delivery system means the end of the delivery system which is first inserted into the patient, i.e., the leading end of the delivery system, and the direction towards the leading end. The terms "proximal" and "proximally" have the opposite meaning. The proximal and distal directions are indicated in the figures by the arrows "P" and "D" respectively.

Figure 1:
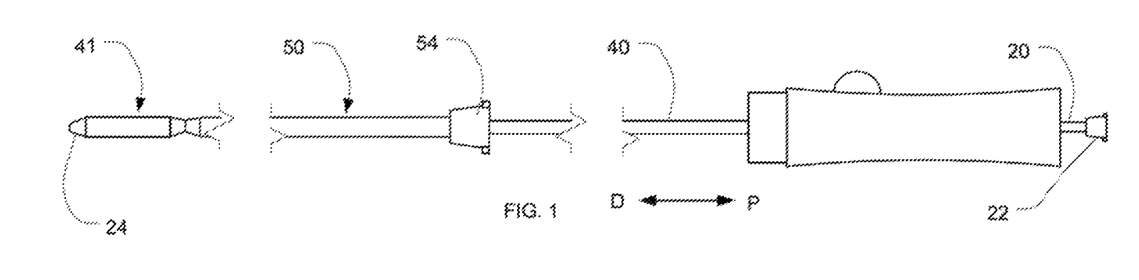
FIG. 1 is a diagrammatic elevational view of a delivery system according to one embodiment of the disclosure.
Figures 2, 3, 4:
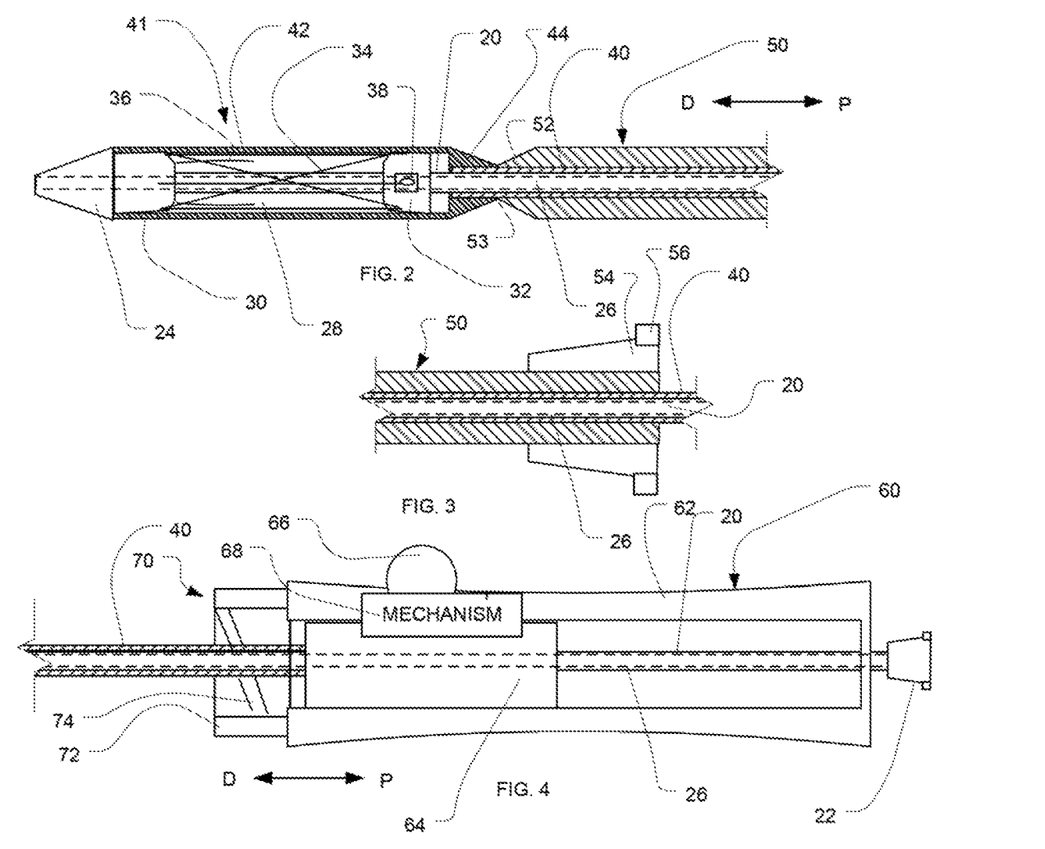
FIGS. 2, 3, and 4 are fragmentary diagrammatic sectional views depicting portions of the system shown in FIG. 1.

A delivery system according to one embodiment (FIGS. 1-5) includes an inner shaft 20 having a hub 22 at a proximal end 22 of the shaft. Inner shaft 20 also includes a tip 24 at the distal end of the shaft. Tip 24 has a larger diameter than the main portion of the shaft and tapers in the distal direction. The inner shaft has a lumen 26 depicted in broken lines in FIGS. 2-4 extending the entire length of the shaft. The inner shaft has a device-carrying region 28 just proximal to the tapered tip 24. Desirably, the inner shaft is provided with features such as a distal collar 30 connected to tip 24 and a proximal collar 32 in the device-carrying region 28. One or both of these collars may be provided with features adapted to hold a collapsible implantable device in place relative to the inner shaft and prevent the device from moving proximally or distally relative to the shaft while the device is in a collapsed condition. The particular implantable device depicted in FIG. 2 is a prosthetic heart valve assembly including a stent 34 and valve leaflets 36 attached to the stent. In the particular example shown, a tab 38 is received in a pocket in the proximal collar 32 of the inner shaft so that the stent cannot move proximally or distally relative to the proximal collar and relative to the inner shaft while the stent remains in the collapsed condition. Other arrangements can be used. For example, one or both of the collars may incorporate projections that engage in spaces between elements of the stent. Also, elements such as sutures can be used to hold the implantable device in place relative to the inner shaft.

An elongated outer shaft 40 surrounds the inner shaft 20 over most of its length. Outer shaft 40 is substantially in the form of a cylindrical tube of constant inside and outside diameters. The outer shaft 40 forms a close but freely slideable fit with the inner shaft. A hollow sheath 41 is mounted to the distal end of outer shaft 40. Sheath includes a main portion which is a tube of substantially constant inside and outside diameters. The inside diameter of main portion 42 is sufficient to accommodate the features of the device-carrying region 28 of the inner shaft, including the collars 32 and 30, and to also accommodate the implantable device in the collapsed state shown in FIG. 2. The outside diameter of main portion 42 is larger than the outside diameter of shaft 40.

The main portion 42 of the sheath is open at its distal end. The sheath has a substantially closed proximal end 44 that tapers in the proximal direction from the outside diameter of main portion 42 to a diameter equal to the diameter of outer shaft 40. Desirably, the surface of proximal end 44 is a surface of revolution such as a cone or a frustum of a cone coaxial with the main portion 42 of the sheath. The sheath 41 is fixed in position at the distal end of the outer shaft 40. For example, the sheath may be formed integrally with the outer shaft or bonded to the outer shaft by gluing, solvent welding, or the like.

An elongated tubular sleeve 50 surrounds outer shaft 40 over a portion of its length. Desirably, the inner bore of sleeve 50 forms a close but freely slideable fit with the outer surface of outer shaft 40. For example, sleeve 50 may have a diameter on the order of 0.002-0.010 inches (50-250 µm) greater than the outside diameter of outer shaft 40. Sleeve 50 desirably has an outside diameter at its distal end (FIG. 2) equal to the outside diameter of the main portion 42 of sheath 41 or slightly less than the outside diameter of main portion 42 of the sheath. The outside diameter of sleeve 50 may be constant or may increase slightly in the proximal direction. At its distal end, sleeve 50 has a distal end portion 52 defining a surface in the form of a cone or a frustum of a cone tapering in the distal direction and concentric with the outside diameter of sleeve 50. The surface defined by distal end portion 52 may be substantially a mirror image of the surface defined by the proximal end 44 of the sheath. The distal end portion 52 of the sleeve abuts the proximal end of the sheath when the sleeve is in its advanced position. Such abutment occurs along a narrow circular zone of abutment 53 surrounding outer shaft 52. When the sleeve 50 is in its advanced position, sleeve 50 and sheath 41 cooperatively define a smooth outer surface which includes a smooth taper from the diameter of sheath main portion 42 to a smaller diameter at the abutment zone 53 and a smooth increase in diameter from the abutment zone to the diameter of cylindrical surface of sleeve 50. Desirably, any gap or indentation in this surface at the abutment zone 53 between the sleeve and the sheath is shallow and small, and any deviation from a perfectly smooth surface has dimensions on the order of less than 1 mm and desirably less than 50 microns. Also, any deviation from a perfectly smooth surface desirably has a rounded profile. A hub 54 (FIGS. 1, 3) is fixed to the sleeve 50 at its proximal end. Hub 54 has projections 56 at its periphery.

A handle 60, best seen in FIG. 4, incorporates a body 62 and an internal carriage 64 movable relative to the body in the proximal and distal directions along the axis of the body. The handle also has a first control element schematically shown at 66, which is mounted to the body and accessible to the user, as well as a mechanism 68 for moving the movable carriage 64 responsive to movement of the control element by the user. For example, in one embodiment, the mechanism may include screw threads (not shown) on the carriage 64 and a nut (not shown) surrounding the carriage engaged with the threads. The control element 66 may include a ring surrounding the nut and exposed at one or more surfaces of handle body 60, so that the user can simply turn the nut. The nut may be a "split" nut that can be opened or closed to engage it or disengage it with the threads, and an additional control (not shown) may be provided for engaging and disengaging the nut. A further control element (not shown) may be provided so that the user can manually slide the carriage 64 using that additional control element, without using the mechanism. Desirably, while the mechanism is engaged with the carriage, the carriage is locked against displacement by loads applied directly to the carriage in the proximal and distal directions, and can only be moved by actuation of the control element. Many other mechanisms are known in the art for moving a carriage within the body of a handle responsive to movement of a control element. These include mechanical linkages such as rack and gear mechanisms, lever systems and the like. Still other mechanisms incorporate pneumatic, hydraulic, or electrical elements for moving the carriage. Any such mechanism can be used. The inner shaft 20 extends through carriage 64, but is not attached thereto. Inner shaft 20 is fixed to body 60 adjacent the proximal end of the inner shaft. The proximal end of outer shaft 40 is fixed to carriage 64. Thus, by actuating control element 66, the user can move the outer shaft 40 and the sheath relative to the inner shaft.

Figure 5:
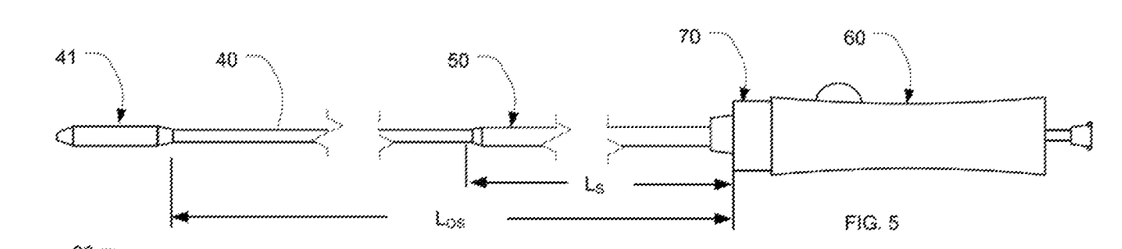
FIGS. 5 and 6 are views similar to FIG. 1, but depicting the delivery system of FIGS. 1-4 in different operating conditions.

A catch 70 includes a hollow collar 72 fixed to body 60 at its forward end and having threads schematically indicated at 74. As further discussed below, catch 70 can be engaged with the hub 54 of sleeve 50 (FIG. 3) by threadedly engaging the projections 56 on the hub with the threads 74 of the catch. The hub 54 of sleeve 50 can be interlocked with catch 70 when the sleeve is in a fully retracted position, as depicted in FIG. 5. The sleeve can also be brought to any intermediate position between the fully advanced position of FIG. 1 and the fully retracted position of FIG. 5. While the sleeve is in the fully retracted position or in a partially retracted position, where the front end of the sleeve is remote from sheath 41, sheath may be retracted proximally relative to the inner shaft 20 by actuating control element 66 to move carriage 64 (FIG. 4) proximally, thus moving outer shaft 40 and sheath 41. In the fully retracted position of sheath 41 (FIG. 6), the device-carrying region 28 of the inner shaft is exposed and the device can expand fully so as to free itself from its engagement with the inner shaft.

Figure 7:
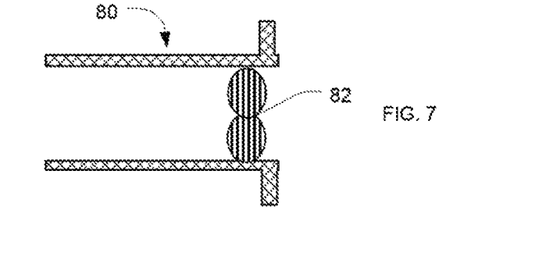
FIG. 7 is a diagrammatic sectional view depicting an introducer that may be used with the delivery system of FIGS. 1-6.

The delivery system optionally can be used in conjunction with an introducer 80. The introducer is a tubular cannula having a resilient elastomeric seal 82 mounted in a bore of the tubular element. The resilient elastomeric seal may be of any form, such as a slit sheet of rubber or other elastic material, or an o-ring or other gasket capable of providing a substantially blood-tight seal between the introducer and sleeve 50. Desirably, the hub 54 of sleeve 50 is dimensioned so that it cannot pass through the introducer.

Figure 6:
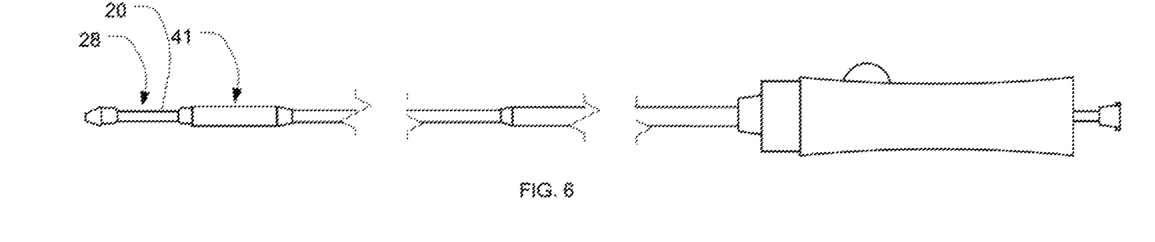

Sleeve 50 is shorter than outer shaft 40. For example, when sleeve is in its fully retracted position and engaged with catch 70, and when the sheath and outer shaft are in the advanced position as shown in FIG. 5, the length $L_S$ of the sleeve projecting from the front end of the handle 60 and catch 70 may be about 20 to about 40 cm less than the length $L_{OS}$. The length $L_{OS}$ of the outer shaft is measured between the most distal point of the handle or catch and the most distal point on the sheath that is engaged by the sleeve when the sleeve is in its advanced position (FIG. 1). Thus in the condition as depicted in FIG. 5, the distal end of sleeve 50 desirably is at least 15 cm proximal to the sheath and more preferably about 20 cm to about 40 cm proximal to the sheath. This spacing is substantially greater than the distance through which the sheath 41 moves from the advanced position (FIG. 5) to the retracted position (FIG. 6). In one embodiment intended for placement of a valve in the aortic annulus of an adult human, the length $L_S$ of the sleeve 50 may be on the order of 70 cm, whereas the length $L_{OS}$ of outer shaft 40 may be on the order of 100 cm. The sleeve 50 and the main portion of sheath 41 may have a diameter of about 18 French (6 mm), whereas outer shaft 40 may have a diameter of about 12 French to about 14 French (4.33 mm).

The shaft, sleeve, and sheath can be formed from medically acceptable polymeric materials. Desirably, the materials are selected so that the inner and outer shafts have sufficient flexibility to accommodate the bending encountered in operation, and to provide low-friction, easily slideable engagement between the inner and outer shafts and between the outer shaft and the sleeve. The sleeve may be somewhat stiffer than the inner and outer shafts.

In a method of operation according to a further aspect of the disclosure, an implantable device such as a prosthetic heart valve is implanted in a subject at a delivery location DL (FIG. 8) that is in the vicinity of the aortic annulus of the heart H. In preparation for the method, introducer 80 is inserted into the subject's vasculature through an entry site at the subject's groin, into the femoral artery FA (FIG. 8) using conventional technique. A guidewire 90 is placed through the introducer and advanced using a conventional technique through the femoral artery FA, the iliac artery IA and abdominal aorta AB, and around the arch of the aorta, and passed through the aortic annulus into the heart H.

The implantable device and the delivery system are brought to the condition shown in FIGS. 1-4, with the outer shaft 40 and sheath 41 in their fully advanced position relative to the inner shaft 20, so that the sheath 41 covers the implantable device, and with the sleeve 50 in its fully advanced position, abutting the proximal end 44 of the sheath. With the device in this condition, the device is threaded over the proximal end of the guidewire, so that the proximal end of the guidewire enters the distal end of lumen 26 (FIG. 2) of the inner shaft through tip 24. The physician grasps handle 60 and advances the delivery system into the vasculature through the introducer 80 with tip 24 leading. During the initial stages of the advance, the physician maintains the sleeve 50 in its fully advanced condition and engaged with the sheath as, for example, by grasping the sleeve 50 and urging the sleeve forward. The physician may also apply distally directed force on the handle. The smooth transition between the outer surfaces of the sheath and the sleeve facilitates insertion of the sleeve through the elastomeric seal of the introducer. The physician may continue to advance the introducer along with the inner and outer shafts, so as to maintain the sleeve in its fully advanced position relative to the sheath, until the hub 54 of the sleeve is disposed adjacent the introducer. In this stage, the smooth transition between the outer surfaces of the sheath and the sleeve facilitates advancement of the delivery system and minimizes trauma to the arteries. When the hub of the sleeve encounters the introducer, forward movement of the sleeve is stopped.

Figure 8:
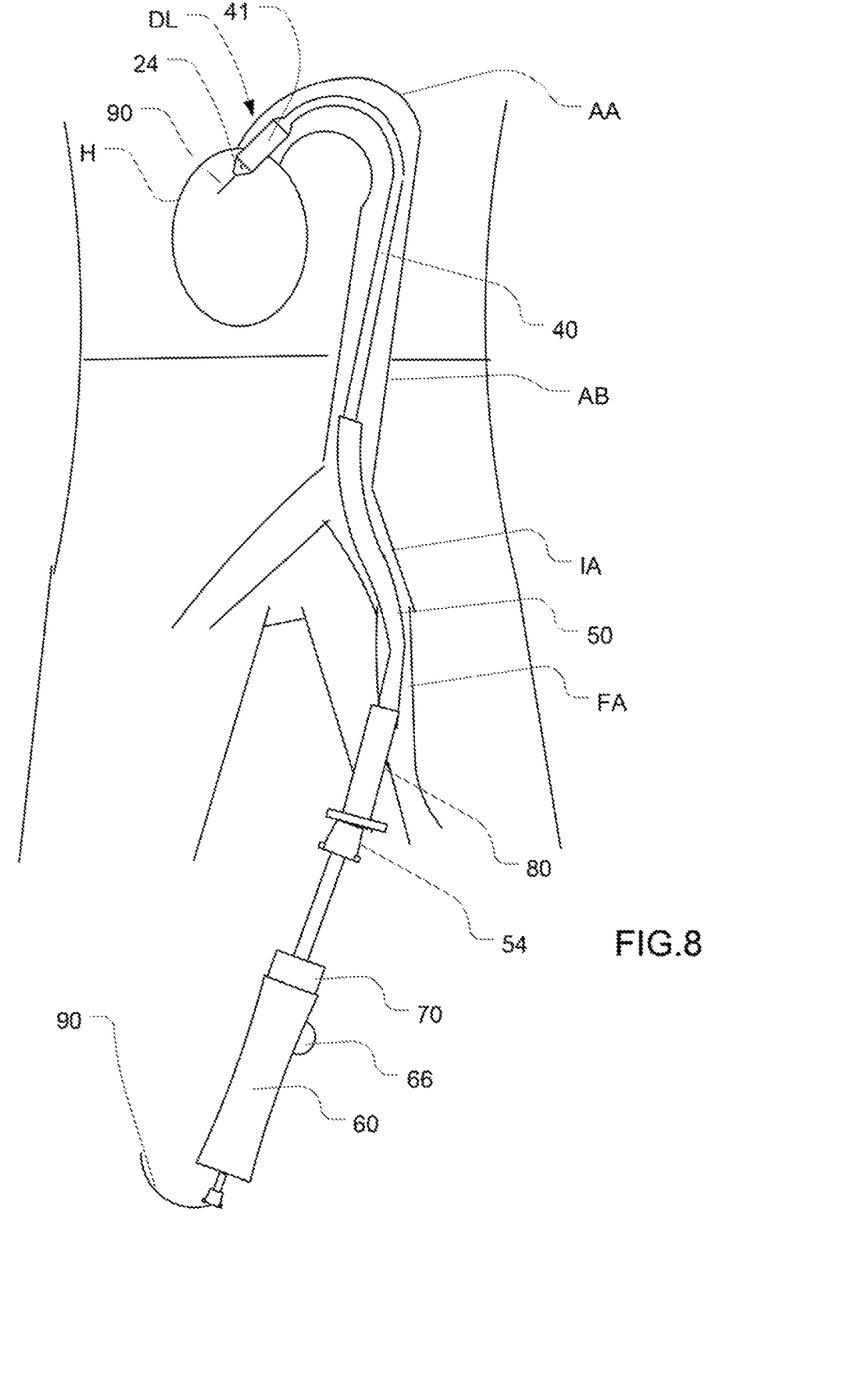
FIG. 8 is a diagrammatic view depicting the delivery system of FIGS. 1-6 and introducer of FIG. 7 in operation in conjunction with a human subject.

At this point, the distal end of the sleeve is disposed in the abdominal aorta AB, remote from the aortic arch AA. The physician continues to advance the inner and outer shafts by moving the handle 60. The outer shaft slides readily through the sleeve. By the time the distal end of the delivery system (tip 24) approaches the aortic arch, a substantial portion of the outer shaft 40 is disposed distal to the sleeve. This portion of the outer shaft can bend readily because it is not constrained by the sleeve. Thus, the device can follow or "track" the guidewire as it traverses the bend of the aortic arch. Continued advancement brings the sheath 41 and the device-carrying region of the inner shaft to the desired delivery location DL, near the aortic annulus. The free sliding motion of the outer shaft 40 within the sleeve 50 facilitates precise positioning at the delivery location. The physician typically confirms proper positioning by fluoroscopic imaging and makes any necessary adjustments. At this stage of the procedure, the hub 54 of the sleeve typically is disposed distal to the catch 70 on handle 60, as depicted in FIG. 8. Stated another way, the sleeve is in a partially retracted position relative to the inner and outer shafts.

While holding the handle steady to maintain the position of the implantable device, the physician can grasp sleeve 50, as by grasping hub 54, and can pull the hub and sleeve proximally to bring the sleeve to its fully retracted position and engage the hub with catch 70. Although the introducer and the tissues of the subject bearing on the sleeve exert appreciable frictional forces on the sleeve, the sleeve slides freely over the outer shaft 40 of the delivery system. Once hub 54 is fixed to catch 70, the handle is locked to the sleeve.

After locking the handle to the sleeve, the physician actuates the control element 66 to retract the outer shaft 40 relative to the inner shaft and relative to the implantable device. The physician holds handle 60 steady during this step, so as to assure that the inner shaft and the implantable device remain stationary while the outer shaft 40 and sheath 41 move relative to the subject. The frictional forces exerted on sleeve 50 by the seal of introducer 80 and by tissues in contact with the sleeve help to keep the handle stationary. This is directly opposite to the effect which would occur if the delivery system was used without sleeve 50, so that outer shaft 40 was in direct contact with the seal of the introducer. In that case, the frictional forces exerted by the introducer seal and the tissues adjacent the entry site would tend to hold the outer shaft stationary. This would force the handle and inner shaft to move relative to the subject in response to actuation of the control element, thereby moving the implantable device away from its desired position.

The procedure discussed above can be varied. For example, while the delivery system is being advanced to the delivery location, the physician can stop the distal movement of the sleeve before hub 54 encounters the introducer. Also, the physician can retract the outer sleeve during advancement of the delivery system. Either of these approaches will leave the front end of the sleeve lower in the abdominal aorta or in the iliac artery while the tip 24 and sheath 41 traverse the aortic arch. This in turn further increases flexibility of the leading portion of the outer sheath for tracking along the guidewire through the aortic arch.

In a method according to a further aspect of the disclosure, the delivery system is inserted without placing an introducer at the entry location. The procedures used in this variant are generally the same as those discussed above. Here again, the sleeve desirably is at its advanced position when the delivery system is inserted into the artery at the entry location after placement of the guidewire. The smooth transition between the outer surface of the sheath and the outer surface of the sleeve facilitates advancement of the delivery system through the tissues at the entry location, and helps to minimize trauma. Moreover, when the sleeve in its advanced position, it acts to stiffen the leading portion of the delivery system. This may make it easier to force the delivery system through the tissues at the entry location. The physician may grasp the sleeve at the hub or at another location and urge the sleeve forward during insertion into the artery, thus forcing the sheath and the shafts distally.

This motion is continued at least until the front end of the sleeve enters the artery. In this method as well, the physician may continue moving the sleeve forwardly until the hub of the sleeve reaches the subject's skin, or may stop moving the sleeve forwardly at a desired location. Here again, the sleeve desirably is retracted and locked to the handle after the implantable device reaches the desired delivery location. Because the sleeve is forcibly engaged by tissues at the entry location, the sleeve will again help to hold the handle stationary while the outer sheath is retracted to expose the implantable device.

Omission of the introducer can allow use of a larger diameter sheath and sleeve in an artery of a given size at the entry location. Where an introducer is used, the introducer must have an outside diameter small enough to fit within the artery at the entry location. The diameters of the sheath and sleeve must be less than the inside diameter of the introducer. Where the introducer is omitted, the diameters of the sheath and sleeve are limited only by the diameter of the artery.

In the embodiments discussed above, the sleeve abuts the proximal end of the sheath when the sleeve is in the advanced position. In other embodiments, distal movement of the sleeve may be limited by a projection (not shown) on the outer shaft or by a thin spacer overlying the proximal end of the sheath. In these embodiments, the distal end of the sleeve should be in close proximity to the proximal end of the sheath, so that the sheath and sheath, with or without any intervening spacer element, cooperatively define a smooth outer surface as discussed above.

In the embodiments discussed above, the implantable device is self-expanding. However, in other embodiments a balloon or other expandable element is provided on the inner shaft in the device-carrying region, and is used to expand the implantable device after retraction of the sheath.

Figure 9:
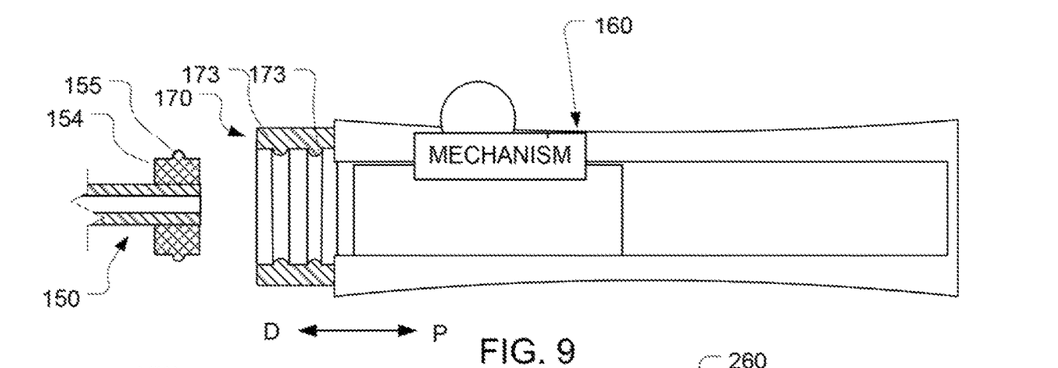
FIG. 9 is a view similar to FIG. 4, but depicting portions of a delivery system in accordance with a further embodiment of the disclosure.

The catch on the handle and the hub on the sleeve can be varied. For example, a catch in the form of a threaded collar such as collar 72 (FIG. 4) may be mounted to the handle so that the catch is rotatable about its axis, but fixed against proximal and distal movement relative to the handle. The catch need not be threaded. For example, a handle 160 according to a further embodiment (FIG. 9) has a catch 170 in the form of a collar with inwardly projecting ribs 173. The hub 154 of the sleeve 150 may have projections 155. The hub can be engaged with the catch by forcing the hub into the collar until the projections on the hub pass the first projection 173 of the collar and snap into the space between the projections of the collar. Such engagement will lock the hub and hence sleeve 150 against proximal and distal motion relative to the housing, but may allow rotation of the housing relative to the sleeve.

In a further embodiment, the hub may have a tapered, conical portion (not shown), whereas the catch may include a tapered opening (not shown). The conical portion of the hub can be locked to the catch by forcing it into the opening so as to frictionally engage the hub with the catch.

Figure 10:
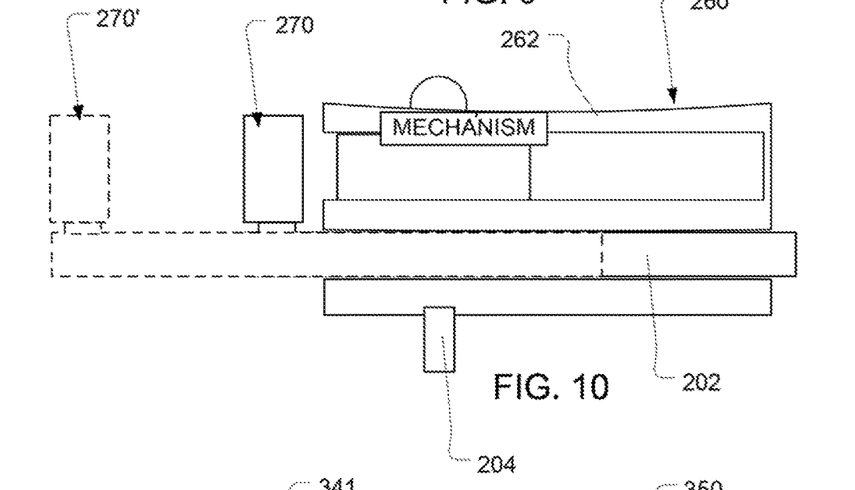
FIG. 10 is a view similar to FIG. 9, but depicting portions of a delivery system according to yet another embodiment of the disclosure.

In yet another embodiment (FIG. 10), the catch 270 may be mounted to the body 262 of the handle 260 through a link 202. The link and catch may be movable proximally and distally relative to the body of the handle when a stop element 204 mounted to the body is in an unlock position, and may be fixed against such movement when the stop element is in a lock position. The link and catch may be moved distally relative to the body of the handle as indicated in broken lines at 270' to engage the catch with the hub of the sleeve, and then the stop may be brought to the lock position so that the hub of the sleeve is fixed relative to the body of the handle. In a further variant, a mechanism (not shown) similar to the mechanism 68 discussed above with reference to FIG. 4 may be provided for moving the link and catch proximally and distally relative to the handle body in a controllable manner.

Figure 11:
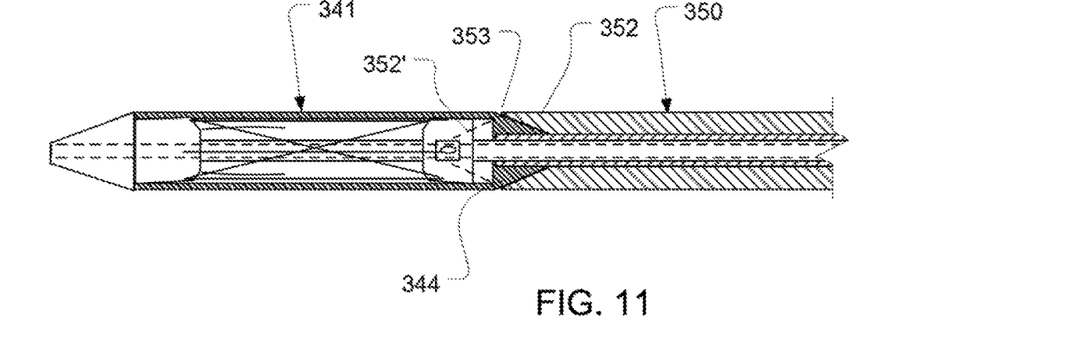
FIG. 11 is a view similar to FIG. 2, but depicting portions of a delivery system according to a still further embodiment of the disclosure.

The configuration of the proximal end of the sheath and the distal end of the sleeve can be different from the particular configuration depicted in FIG. 2. For example, a delivery system according to a further embodiment incorporates a sheath 341 having a proximal end 344 defining a conical outer surface tapering in the proximal direction, similar to the sheath shown in FIG. 2. Sleeve 350 has a distal end defining an internal conical surface complimentary to the surface of the sheath distal end. In this embodiment, the sheath and sleeve fit together so as to form a substantially continuous cylindrical outer surface with only a very small indentation at the abutment zone. The reverse arrangement, with the proximal end of the sheath defining the internal surface and the distal end of the sleeve defining the external surface, also can be used. Also, the abutting surfaces need not be conical. Desirably, the abutting surfaces are surfaces of revolution about the proximal-to-distal axis so as to maintain concentricity between the outer surfaces of the sleeve and sheath. In either arrangement, the end of the sleeve or sheath which defines the internal surface may be deformable so that such end is deformed to form the internal surface when the parts are brought into abutment, but reverts to an external surface when the parts are out of abutment. For example, the distal end 352 may have the shape indicated in solid lines in FIG. 11 when the parts are in abutment, but may revert to a shape defining an external taper as shown in broken lines at 352' when the parts or remote from one another. A similar arrangement may be used on the proximal end of the sheath where the sheath defines the internal surface. As these and other variations and combinations of the features set forth above may be used, the foregoing description should be taken as illustrative rather than as limiting the disclosure.

The invention claimed is:

1. A delivery system for an implantable medical device, the delivery system comprising:
   (a) an elongated inner shaft having a device-carrying region adjacent a distal end thereof;
   (b) an elongated, hollow outer shaft surrounding the inner shaft;
   (c) a sheath mounted at a distal end of the outer shaft, the sheath having an outside diameter greater than an outside diameter of the outer shaft, the outer shaft being movable relative to the inner shaft in a proximal direction from an advanced position in which the sheath surrounds the device-carrying region of the inner shaft to a retracted position in which the sheath does not cover the device-carrying region; and
   (d) a sleeve shorter than the outer shaft, the sleeve surrounding the outer shaft, the sleeve being movable relative to the outer shaft from an advanced position in which a distal end of the sleeve is in close proximity to a proximal end of the sheath to a fully retracted position in which the distal end of the sleeve is remote from the sheath, the distal end of the sleeve and the sheath cooperatively defining a smooth exterior surface when the sleeve is in the advanced position, wherein the distal end of the sleeve has an outside diameter substantially equal to an outside diameter of a portion of the sheath disposed adjacent the proximal end thereof, and when the sleeve is in the advanced position, the distal end of the sleeve and the proximal end of the sheath fit together so as to form a substantially continuous cylindrical outer surface, and wherein a first end, which is one of the distal end of the sleeve or the proximal end of the sheath, is deformable so that the first end is deformed when the sleeve is in the advanced position.

2. A delivery system as claimed in claim 1 wherein the sheath and the distal end of the sleeve are concentric with one another when the sleeve is in the advanced position.

3. A delivery system as claimed in claim 2 wherein the sheath has a proximal end surface that tapers in the proximal direction and wherein the sleeve abuts the proximal end surface when the sleeve is in the advanced position.

4. A delivery system as claimed in claim 1 wherein, when the sleeve is in the fully retracted position and the sheath is in the advanced position, the distal end of the sleeve is at least 15 cm proximal to the sheath.

5. A delivery system as claimed in claim 4 wherein, when the sleeve is in the fully retracted position and the sheath is in the advanced position, the distal end of the sleeve is between 20 and 40 cm proximal to the sheath.

6. A delivery system as claimed in any of claim 1 or 2-5 further comprising a handle having a body and a control element, a proximal end of the inner shaft being fixed to the body, the outer shaft being movable relative to the inner shaft responsive to movement of the control element.

7. A delivery system for an implantable medical device, the delivery system comprising:
    (a) an elongated inner shaft having a device-carrying region adjacent a distal end thereof;
    (b) an elongated, hollow outer shaft surrounding the inner shaft;
    (c) a sheath mounted at a distal end of the outer shaft, the sheath having an outside diameter greater than an outside diameter of the outer shaft, the outer shaft being movable relative to the inner shaft in a proximal direction from an advanced position in which the sheath surrounds the device-carrying region of the inner shaft to a retracted position in which the sheath does not cover the device-carrying region;
    (d) a sleeve shorter than the outer shaft surrounding the outer shaft, the sleeve being movable in a proximal direction relative to the outer shaft from an advanced position to a fully retracted position in which a distal end of the sleeve is remote from the sheath;
    (e) a handle having a body and a first control element, the inner shaft being fixed to the body, the outer shaft being movable relative to the inner shaft responsive to movement of the control element relative to the body by an operator; and
    (f) a catch operable to selectively fix the sleeve to the body of the handle against proximal and distal movement relative to the body when the sleeve is in the fully retracted position, wherein the distal end of the sleeve has an outside diameter substantially equal to an outside diameter of a portion of the sheath disposed adjacent a proximal end thereof, and when the sleeve is in the advanced position, the distal end of the sleeve and the proximal end of the sheath fit together so as to form a substantially continuous cylindrical outer surface, and wherein a first end, which is one of the distal end of the sleeve or the proximal end of the sheath, is deformable so that the first end is deformed when the sleeve is in the advanced position.

8. A delivery system as claimed in claim 7 wherein the sleeve includes a hub fixed to the sleeve adjacent its proximal end, the hub and catch being engageable with one another to fix the sleeve to the body.

9. A delivery system as claimed in claim 7 further comprising a link mounted to the body, and a stop mounted to the body and selectively movable from an unlock position and a lock position, the link being movable relative to the body when the stop is in the unlock position, the link being fixed relative to the body when the stop is in the lock position, the catch being mounted to the link.

10. A delivery system as claimed in claim 7 or claim 9 wherein the handle includes a second control element, the link being movable responsive to movement of the second control element by an operator.

\* \* \* \* \*